(12) United States Patent
Robinson et al.

(10) Patent No.: US 9,189,704 B2
(45) Date of Patent: Nov. 17, 2015

(54) KERNEL WITH ITERATIVE COMPUTATION

(71) Applicant: RAYTHEON COMPANY, Waltham, MA (US)

(72) Inventors: Ian S. Robinson, Redondo Beach, CA (US); Bradley A. Flanders, Whitier, CA (US); Anthony Sommese, Port Jefferson, NY (US)

(73) Assignee: RAYTHEON COMPANY, Waltham, MA (US)

( * ) Notice: Subject to any disclaimer, the term of this patent is extended or adjusted under 35 U.S.C. 154(b) by 393 days.

(21) Appl. No.: 13/870,685

(22) Filed: Apr. 25, 2013

(65) Prior Publication Data

US 2014/0321697 A1  Oct. 30, 2014

(51) Int. Cl.
*G06K 9/62* (2006.01)
*G01N 21/31* (2006.01)
*G01J 3/28* (2006.01)
*G06K 9/00* (2006.01)
*G01N 21/17* (2006.01)
*G06K 9/46* (2006.01)

(52) U.S. Cl.
CPC ............. *G06K 9/6202* (2013.01); *G01J 3/28* (2013.01); *G01N 21/31* (2013.01); *G06K 9/00536* (2013.01); *G01N 2021/1793* (2013.01); *G06K 2009/00644* (2013.01); *G06K 2009/4657* (2013.01); *G06T 2207/10036* (2013.01)

(58) Field of Classification Search
CPC .......... G06T 2207/10032; G06T 2207/10036; G06K 2009/4657; G06K 2209/00644; G06K 9/00624; G06K 9/0063; G01N 2223/423; G01J 2003/2826

USPC .................................. 382/103, 190, 191
See application file for complete search history.

(56) References Cited

U.S. PATENT DOCUMENTS

| 6,466,961 | B1 * | 10/2002 | Miller ........................... 708/816 |
| 7,194,111 | B1 * | 3/2007 | Schaum et al. ............... 382/103 |
| 2006/0188161 | A1 * | 8/2006 | Gruninger et al. ............ 382/191 |
| 2006/0233421 | A1 * | 10/2006 | Portigal et al. ................ 382/103 |
| 2009/0074297 | A1 * | 3/2009 | Robinson ...................... 382/191 |
| 2010/0288910 | A1 * | 11/2010 | Robinson et al. ........... 250/208.1 |
| 2011/0221926 | A1 * | 9/2011 | Kanaev et al. ............. 348/222.1 |

OTHER PUBLICATIONS

Kwon, et al. "Kernel RX-Algorithm: A Nonlinear Anomaly Detector for Hyperspectral Imagery." IEEE Transactions on Geoscience and Remote Sensing. 43.2 (2005): 388-397. Print.*

(Continued)

*Primary Examiner* — Michael A Newman
(74) *Attorney, Agent, or Firm* — Burns & Levinson LLP; Joseph M. Maraia

(57) ABSTRACT

Provided are examples of a detecting engine for determining in which pixels in a hyperspectral scene are materials of interest or targets present. A collection of spectral references, typically five to a few hundred, is used in look a through a million or more pixels per scene to identify detections. An example of the detecting engine identifies detections by calculating a kernel vector for each spectral reference in the collection. This calculation is quicker than the conventional Matched Filter kernel calculation which computes a kernel for each scene pixel. Another example of the detecting engine selects pixels with high detection filter scores and calculates coherence scores for these pixels. This calculation is more efficient than the conventional Adaptive Cosine/Coherence Estimator calculation that calculates a score for each scene pixel, most of which do not provide a detection.

10 Claims, 5 Drawing Sheets

(56) References Cited

OTHER PUBLICATIONS

Kwon, et al. "Kernel adaptive subspace detector for hyperspectral imagery." IEEE Transactions on Geoscience and Remote Sensing. 3.2 (2006): 271-275. Print.*

Kwon, et al. United States. Army Research Laboratory. Kernel-Based Anomaly Detection in Hyperspectral Imagery. Adelphi: , 2004. Web. <http://www.dtic.mil/cgi-bin/GetTRDoc?AD=ADA431620>.*

Dimitris Manolakis: "Taxonomy of Detection Algorithms for Hyperspectral Imaging Applications", Optical Engineering, vol. 44, No. 6, Jan. 1, 2005, p. 066403.

Karmon Vongsy et al: "A Comparative Study of Spectral Detectors", Hyperspectral Image and Signal Processing: Evolution in Remote Sensing (WHISPERS), 2011 3rd Workshop On, IEEE, Jun. 6, 2011. pp. 1-4.

Manolakis et al., "Is There a Best Hyperspectral Detection Algorithm?", SPIE—Newsroom; pp. 1-3 (2209).

* cited by examiner

KERNEL WITH ITERATIVE COMPUTATION

BACKGROUND

This disclosure relates generally to the field of image processing, and more particularly to an approach for detecting materials in a hyperspectral scene containing a plurality of pixels.

In many conventional image processing scenarios comprising hyperspectral imaging (HSI) systems, hyperspectral sensors collect data of an image from one spatial line and disperse the spectrum across a perpendicular direction of the focal plane of the optics receiving the image Thus a focal plane pixel measures the intensity of a given spot on the ground in a specific waveband. A complete HSI cube scene is formed by scanning this spatial line across the scene that is imaged. The complete HSI cube may be analyzed as a measurement of the spectrum, the intensity in many wavebands, for a spatial pixel. This spatial pixel represents a given spot on the ground in a cross-scan direction for one of the lines at a given time in the scan direction. Spectral information, however, cannot be exploited by simply looking at the HSI datacube. Instead, each spatial pixel spectra (in D dimensions or wavebands) is typically compared with reference spectra.

Matched Filter (MF) and Adaptive Cosine/Coherence Estimator (ACE) are common hyperspectral filters that are used along with Reed-Xiaoli (RX) anomaly detectors to detect the presence of materials in pixels including in a hyperspectral scene (scene pixels).

MF and ACE match an a priori spectrum or "reference spectrum" representative of a material to be detected to a measured scene pixel. MF and ACE are typically provided with a library or collection of reference spectrums, each representative of a different material. As such, MF and ACE compare each reference spectrum to the spectrum of each pixel. For each comparison, MF and ACE each provide a score (viz., MF score and ACE score) indicative of the likelihood that a respective reference spectrum matches the spectrum of a respective scene pixel. The MF score or ACE score is compared against a threshold. In which pixel is the material present is determined based on the comparison. Provided immediately below are the equations for calculating MF and ACE scores as well as an RX score.

$$MF = \frac{(s-\mu_b)^T \sum_b^{-1} (x-\mu_b)}{(s-\mu_b)^T \sum_b^{-1} (s-\mu_b)}$$

$$ACE = \frac{\left[(s-\mu_b)^T \sum_b^{-1} (x-\mu_b)\right]^2}{(s-\mu_b)^T \sum_b^{-1} (s-\mu_b)(x-\mu_b)^T \sum_b^{-1} (x-\mu_b)}$$

$$RX = (x-\mu_b)^T \sum_b^{-1} (x-\mu_b)$$

where:
s=known target spectrum,
x=pixel spectrum,
$\mu_b$=mean background, and
$\Sigma_b$=covariance matrix

SUMMARY

Inspection of the equations for Matched Filter (MF), Adaptive Cosine/Coherence Estimator (ACE), and Reed-Xiaoli (RX) show that there are two terms to evaluate. The first term $(s-\mu_b)\Sigma_b^{-1}(x-\mu_b)$ is used in MF and ACE, the second term $(x-\mu_b)\Sigma_b^{-1}(x-\mu_b)$ is used in RX and ACE. Prior art HSI processors have been designed to detect anomalies using RX and to detect materials with known signatures using MF and/or ACE. As such, prior art systems compute a "kernel", $\Sigma_b^{-1}(x-\mu_b)$, as part of the RX computation then reuse that kernel to speed up subsequent MF and ACE computations. However, more recently, many HSI sensors are only used to detect known signatures, yet, they retain the computation of the kernel shown above. Use of the anomaly filter, RX, is unnecessary when looking for specific materials; however, the RX term is evaluated to calculate ACE.

The prior art calculates $(s-\mu_b)\Sigma_b^{-1}(x-\mu_b)$ and $(x-\mu_b)\Sigma_b^{-1}(x-\mu_b)$ for every pixel. The computational effort is dominated by calculation of two terms. First is the calculation of the spectral covariance $\Sigma_b^{-1}$, and second is multiplying the inverse of the spectral covariance by the spectrum for each pixel $\Sigma_b^{-1}(x-\mu_b)$ to create a "kernel" at each pixel. The terms above are then the dot product of either the reference spectrum or pixel spectrum with this kernel.

For (P) pixels with (D) spectral bands, the spectral covariance calculation requires about ½ PD^2 floating point multiplies and adds (for a symmetric matrix). The kernel calculation requires PD^2 floating point multiplies and adds. Given that a typical value of P is one million and a typical value of D is 100-400, these calculations are very computationally intensive. Accordingly, there is a need to perform these calculations more efficiently with fewer mathematical operations. Meeting this need saves time, and/or processor size, weight and power.

The approach described herein makes several improvements in computational speed and efficiency when detecting materials whose signature is known a priori. This approache preserves performance with no loss for MF or ACE. One of the improvements is to compute detection filter scores for each pixel in a manner that reduces computations; in some cases, by more than ten times. To compute detection filter scores, a new "kernel vector" is created for each spectral reference (reference spectrum). This is in lieu of computing a prior art kernel per scene pixel. A "matched filter" is still applied to each pixel but the filter is now a vector of dimension D for each spectral reference (or a 2-D matrix of dimension L×D for a library of L spectral references) rather than a 2-D matrix kernel of dimension P×D for all of the scene pixels. The final matched filter score requires the same number of dot products for both approaches. Because L<<P, the approach described herein requires many fewer calculations.

Another improvement is to compute coherence scores in a manner that preserves the savings above and does not require extensive computations per pixel. Instead of computing ACE scores for every pixel, as is typically done, the approach computes coherence scores only for those pixels that have a detection filter score above a nominal threshold, which indicates a potential target. This approach is effective because ACE scores are usually used with matched filter scores to make detection decisions, ACE scores are susceptible to false alarms when the RX score is low, which can be common. This type of false alarm can be eliminated using the matched filter score.

In accordance with an example, a method for detecting materials in a hyperspectral scene containing a plurality of pixels. The method includes, in a detecting engine provided with a plurality of reference spectrums each of which includes spectral bands and a spectrum representative of a material, for each reference spectrum of a respective material, determining a kernel vector of detection filter weights containing an element for each spectral band of a subject reference spectrum. The method further includes determining, based on the kernel vector for the subject reference spectrum, a detection filter score for each of the plurality of pixels and subject reference spectrum. The detection filter score being indicative of a likelihood the spectrum of a respective pixel matches the subject reference spectrum associated with the respective material. The method further includes comparing the detection filter scores to a threshold and determining, based on the comparison, in which of the plurality of pixels in the hyperspectral scene the respective material is present.

In accordance with an example, a system for detecting materials in a hyperspectral scene containing a plurality of pixels. The system includes memory having computer executable instructions thereupon and at least one interface receiving a plurality of reference spectrums each of which includes spectral bands and a spectrum representative of a material. The system further includes a detecting engine coupled to the memory and the at least one interface. The computer executable instructions when executed by the detecting engine cause the detecting engine, for each reference spectrum of a respective material, determine a kernel vector of detection filter weights containing an element for each spectral band of a subject reference spectrum. The detecting engine further caused to determine, based on the kernel vector for the subject reference spectrum, a detection filter score for each of the plurality of pixels and subject reference spectrum. The detection filter score being indicative of a likelihood the spectrum of a respective pixel matches the subject reference spectrum associated with the respective material. The detecting engine further caused to compare the detection filter scores to a threshold and determine, based on the comparison, in which of the plurality of pixels in the hyperspectral scene the respective material is present.

In accordance with an example, a tangible computer-readable storage medium having computer readable instructions stored therein for detecting materials in a hyperspectral scene containing a plurality of pixels. The computer readable instructions when executed by one or more processors provided with a plurality of reference spectrums each of which includes spectral bands and a spectrum representative of a material, cause the one or more processors to, for each reference spectrum of a respective material, determine a kernel vector of detection filter weights containing an element for each spectral band of a subject reference spectrum. The one or more processors further caused to determine, based on the kernel vector for the subject reference spectrum, a detection filter score for each of the plurality of pixels and subject reference spectrum. The detection filter score being indicative of a likelihood the spectrum of a respective pixel matches the subject reference spectrum associated with the respective material. The one or more processors further caused to compare the detection filter scores to a threshold and determine, based on the comparison, in which of the plurality of pixels in the hyperspectral scene the respective material is present.

In some examples, any of the aspects above can include one or more of the following features.

In other examples of the method in which the pixels determined based on the comparison are candidate detections, the method further includes determining a coherence score for each of the candidate detections found using the detection filter scores and subject reference spectrum. The coherence score being indicative of a likelihood the spectrum of a respective candidate detection matches the subject spectrum associated with the respective material. The method further includes comparing the coherence scores to a second threshold and determining, based on the comparison, in which of the candidate detections the respective material is present.

In some examples, the method further includes determining a spectral covariance based on the plurality of pixels in the hyperspectral scene. The kernel vector for each reference spectrum is determined using the product of a respective reference spectrum and the inverse of the spectral covariance.

In other examples, the method further includes determining a sample spectral covariance based on a subset of the plurality of pixels in the hyperspectral scene. The kernel vector for each reference spectrum is determined using the product of a respective reference spectrum and the inverse of the sample covariance.

In some examples, the method further includes determining a sample spectral covariance based on a subset of the plurality of pixels in the hyperspectral scene. The coherence scores are determined using the sample spectral covariance.

In other examples of the method, comparing includes combining the detection filter scores and coherence scores into combined scores and comparing the combined scores to the second threshold.

In some examples of the system in which the pixels determined based on the comparison are candidate detections, the detecting engine further caused to determine a coherence score for each of the candidate detections found using the detection filter scores and subject reference spectrum. The coherence score being indicative of a likelihood the spectrum of a respective candidate detection matches the subject spectrum associated with the respective material. The detecting engine further caused to compare the coherence scores to a second threshold and determine, based on the comparison, in which of the candidate detections the respective material is present.

In other examples of the tangible non-transitory computer-readable storage medium in which the pixels determined based on the comparison are candidate detections, the one or more processors caused to determine a coherence score for each of the candidate detections found using the detection filter scores and subject reference spectrum. The coherence score being indicative of a likelihood the spectrum of a respective candidate detection matches the subject spectrum associated with the respective material. The one or more processors further caused to compare the coherence scores to a second threshold and determine, based on the comparison, in which of the candidate detections the respective material is present.

These and other features and characteristics, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various Figures. It is to be expressly understood, however, that the drawings are for the purpose of illustration and description only and are not intended as a definition of the limits of claims. As used in the specification and in the claims, the singular form of "a", "an", and "the" include plural referents unless the context clearly dictates otherwise.

BRIEF DESCRIPTION OF THE DRAWINGS

The foregoing and other objects, features and advantages will be apparent from the following more particular description of the examples, as illustrated in the accompanying drawings in which like reference characters refer to the same parts throughout the different views. The drawings are not necessarily to scale, emphasis instead being placed upon illustrating the principles of the examples.

DETAILED DESCRIPTION

Figure 1:
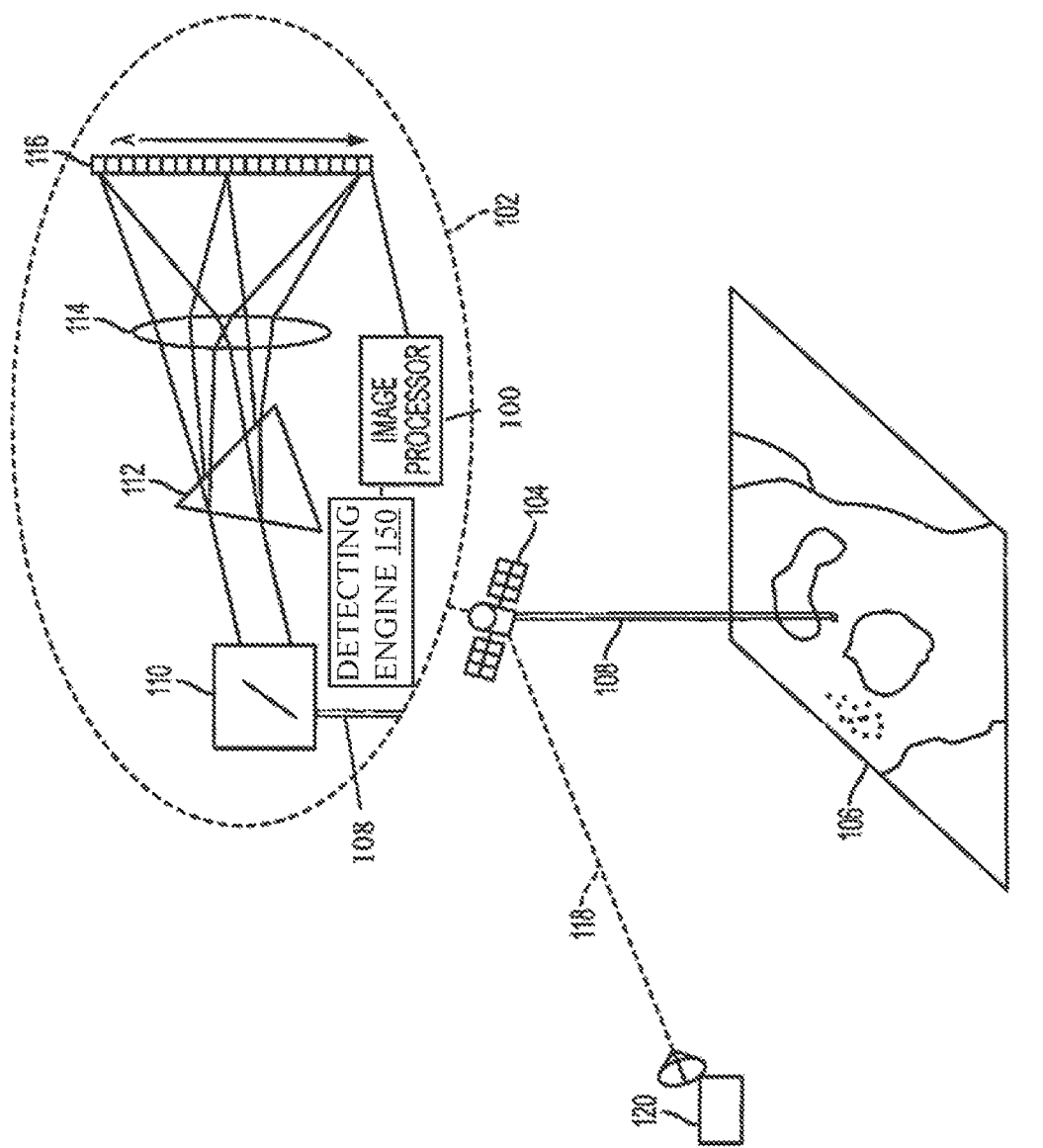
FIG. 1 is a block diagram of an example imaging system with a detecting engine.

In the description that follows, like components have been given the same reference numerals, regardless of whether they are shown in different examples. To illustrate an example (s) of the present disclosure in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

Depicted in FIG. 1 is an example of imaging system 102 that is configured to process images and to detect materials/targets in backgrounds/scenes. By way of example only, imaging system 102 may be a hyperspectral imaging system. The term "hyperspectral" refers to imaging narrow spectral bands over a continuous spectral range, and producing the spectra of all pixels in a scene (e.g., scene 106). Imaging system 102 may be stationary or mobile, airborne or land based (e.g., on an elevated land structure or building), or may be on an aircraft or a satellite. As shown, imaging system 102 may incorporate image processor 100, and may be coupled to or otherwise contained within remote imaging system 104. Remote imaging system 104 may be of any suitable construction or configuration, including but not limited to comprising a satellite, an aerial surveillance system, or any other system that can capture images. Additionally, remote imaging system 104 may be stationary or mobile. In an example, imaging system 102 and remote imaging system 104 may be configured to capture one or more images of a particular scene 106 corresponding to a geographical area (e.g., a ground terrain).

In an example, remote imaging system 104 may be configured to use imaging system 102 to capture hyperspectral image(s) of scene 106 that are provided as input hyperspectral image (HSI) scenes to image processor 100. In an example, hyperspectral imaging system 102 may include one or more scan mirrors 110, or may include other optics arranged to receive light 108 reflected from one or more ground resolution cells. Light 108 reflected from one or more ground resolution cells, and generally the entire scene 106, may be used by image processor 100 to determine an input reflectivity of input HSI scene. Input HSI scene may be a part of scene 106, or may be the entire scene 106 depending upon specific target detection goals. In an example, scan mirrors 110 or the other optics may then direct light 108 through dispersing element 112, which may be arranged to separate light 108 into various different wavelengths (i.e., a spectra). After being separated into the various different wavelengths, light 108 may then be directed to one or more imaging optics 114, which may focus the various wavelengths onto a focal plane of detector array 116. As such, detector array 116 may capture hyperspectral data across the spectrum of wavelengths, thereby generating a data set corresponding to a hyperspectral image of scene 106.

As shown, the imaging system 102 includes a detecting engine 150 for detecting a target in a scene, such as a material against a background. HSI sensors typically collect 200-400 narrow spectral bands over a given sensing regime (e.g., visible and near infra-red (VNIR)/short wave infrared (SWIR) and long wave infrared (LWIR)).

An HSI scene may be composed of 1,000,000 pixels, each of which contains a measured spectrum; typical processing applies many operations to each pixel for detection. The non-literal nature of HSI requires many processing steps for every measured pixel where the processing steps are often vector or matrix operations. There is a strong need to make processing by the detecting engine 150 more computationally efficient.

Figure 2:
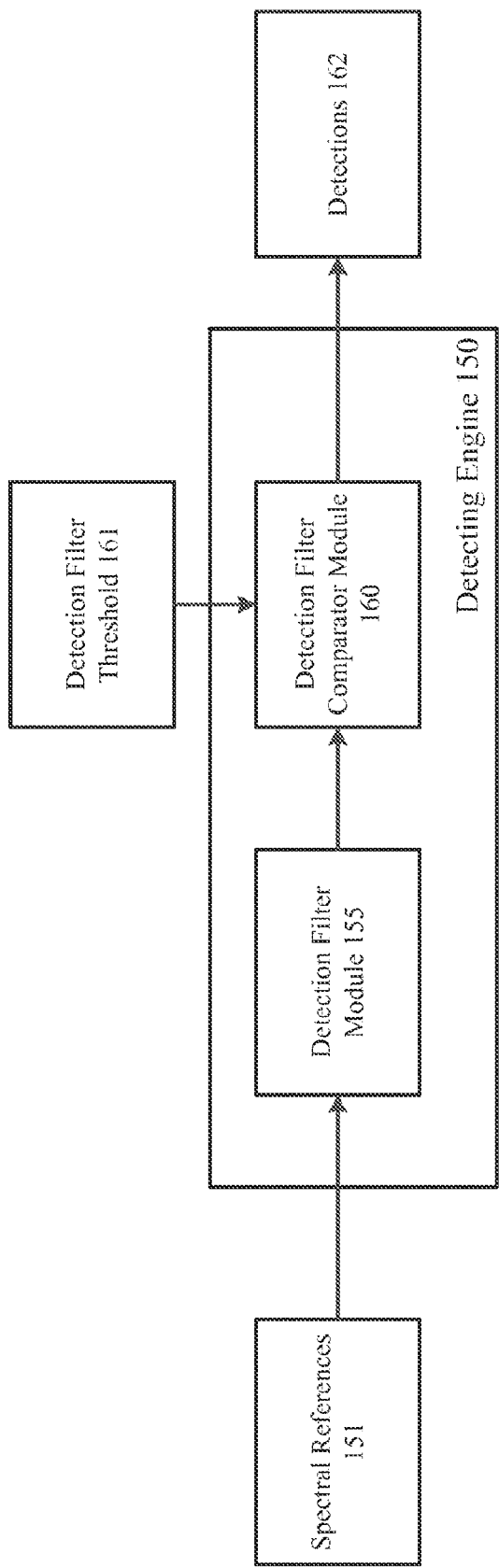
FIG. 2 is a block diagram of an example of the detecting engine.

FIG. 2 shows an example of the detecting engine 150 for detecting materials in a hyperspectral scene having a plurality of pixels. The detecting engine 150 includes a detection filter module 155 communicatively coupled to a detection filter comparator module 160. A plurality of spectral references 151 (reference spectrums) included in the hyperspectral scene are provided to the detecting engine 150 as input. Each spectral reference represents a different material. The detecting engine 150 compares each of the spectral references 151 to each spectrum of each pixel to determine which materials are present in which pixels. For discussion purpose, the operation of the detecting engine 150 is described in context of detecting one material or target of interest.

The detection filter module 155 calculates a kernel vector of detection filter weights containing an element for each spectral band for a reference spectrum representing a material. One of the advantages to the kernel vector is that is computed in fewer operations than the standard MF kernel of the conventional MF approach. The detection engine 150 calculates a kernel vector for each spectral reference (L) in $LD^2$ operations (where D is the number of wavebands). In contrast, a conventional detecting engine calculates a standard MF kernel for each pixel (P) in the hyperspectral scene in $PD^2$ operations (where D is the number of wavebands). The number of spectral reference (L) is typically 5 to a few hundred. The number of pixels, on the other hand, is typically one million or more. As such, the kernel vector calculation is quicker than standard MF kernel calculation by several orders of magnitude.

In a convenient example, the detecting engine 150 multiples each kernel vector (spectral reference vector) by $\Sigma_b^{-1}$ and then by pixels. The order of operations of the detecting engine 150 is the opposite of the order of a conventional MF filter which matrix multiplies $\Sigma_b^{-1}$ to each demeaned pixel vector, $(x-\mu_b)$, forming a kernel of $\Sigma_b^{-1}(x-\mu_b)$ at each pixel. This kernel is then applied to each pixel. The detecting engine 150 creates multiple kernel vectors, one per spectral references 151 rather than a single kernel vector per pixel. Note that the conventional kernel is required to calculate the RX or ACE score at every pixel, but it is not required for the detection filter score.

The detection filter module 155 determines, based on the kernel vector, a detection filter score for each of the plurality of pixels and the reference spectrum. The detection filter score is an indicator of how likely the spectrum of a respective pixel matches the reference spectrum for the material.

The detection filter comparator module 160 receives the detection filter scores from detection filter module 155. The detection filter comparator module 160 compares the detection filter scores to a detection filter threshold 161, also referred to as "detection filter thresholding." The detection filter threshold 161 may be set by a user of the image processor 100, e.g., using the front end interface described with reference to FIG. 1. The detection filter threshold 161 may be predetermined, e.g., based on a desired detection sensitivity. The detection filter threshold 161 may be determined based on criticality application, e.g., detecting explosive is more critical than detecting vegetation.

Based on the detection filter thresholding described above, the detection filter comparator module 160 determines in which of the plurality of scene pixels the material of interest is present. Each such determination is a detection 162. The detecting engine 150 outputs the detections 162, which may be reported to the analysts or recorded for later analysis. Because the kernel vector calculation requires fewer operations, the detecting engine 150 returns detections 162 more quickly than a conventional detecting engine using the standard MF kernel. The foregoing is advantageous for providing real-time or near real-time detection capability. The foregoing is particularly advantageous when the detections are candidate detections for another hyperspectral filter to speed up its processing, which is normally slow.

MF can be combined with ACE to improve detection capability. The false alarm for MF tends to be different then the false alarm for ACE. Because MF scales with the pixel "magnitude," MF false alarms tend to be pixels far from the mean spectrum. Because ACE is independent of pixel magnitude, due to the RX term in the denominator; ACE false alarms tend to be pixels near the mean spectrum (due to small RX values in the denominator).

The conventional approach to detecting materials with ACE involves computing an ACE score for each pixel in the hyperspectral scene. A "flat" or constant threshold is then applied, individually, to each of the ACE scores to determine detection results. The conventional approach is very computational intensive. A typical hyperspectral scene includes one million or more pixels. Computing an ACE score of each of these pixels and then thresholding these scores requires many operations. Current state-of-the-art detecting engines are taxed by the conventional approach. Furthermore, the conventional approach is inefficient because most scene pixels are not detections.

Figure 3:
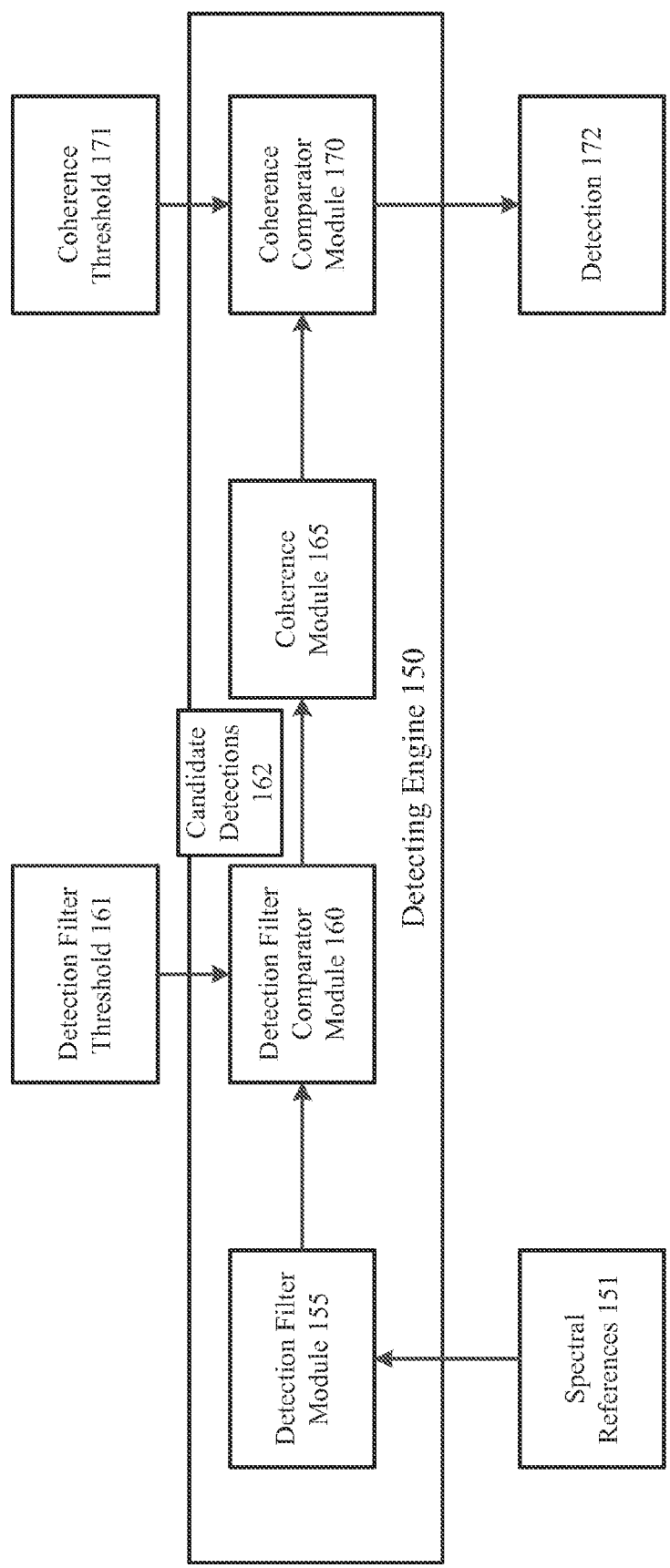
FIG. 3 is a block diagram of another example of the detecting engine.

FIG. 3 shows an example of the detecting engine 150 that reduces the number of operations by selecting a subset of scene and performing coherence estimation on the selected subset. The detecting engine 150 includes the detection filter module 155 and detection filter comparator module 160 from the example described with reference to FIG. 2. The detecting engine 150 further includes a coherence module 165 and coherence comparator module 170. Each of the foregoing modules is communicatively coupled to the other as shown.

A plurality of spectral references 151 are provided to the detecting engine 150 as input. The detecting engine 150 performs the detection filter thresholding using the quicker kernel vector calculation to identify detections 162, as described above. For discussion purpose, the operation of the detecting engine 150 is described in context of detecting one material or target of interest.

The detections 162 are provided to the coherence module 165 as candidate detections 162. The number of candidate detections 162 is much less than the number of scene pixels. The candidate detections 162 are pixels that are likely to have the material of interest present based on their detection filter scores. The candidate detections 162, however, may be false alarms, e.g., false targets. The detecting engine 150 advantageously, verifies or confirms that a candidate detection is a real detection.

The coherence module 165 determines a coherence score for each of the candidate detections 162 and spectral reference. The coherence score is indicative of a likelihood the spectrum of a respective candidate detection matches the spectrum representative of the material of interest. The detecting engine 150 is efficient because instead of scoring all scene pixels, most of which are not detections; the detecting engine 150 computes coherence score for those scene pixels that are likely to be detections.

The coherence comparator module 170 compares the coherence scores to a coherence threshold 171, also referred to as "coherence thresholding." The coherence threshold 171 maybe different that the detection filter threshold 161. The coherence threshold 171 may be set by a user of the image processor 100, e.g., using the front end interface described with reference to FIG. 1. The coherence threshold 171 may be predetermined, e.g., based on a desired detection sensitivity. The coherence threshold 171 may be determined based on criticality application, e.g., detecting explosive is more critical than detecting vegetation.

Based on the coherence thresholding described above, the coherence comparator module 170 determines in which of the plurality of pixels in the hyperspectral scene the material is present. Each such determination is a detection 172. The detecting engine 150 outputs the detections 172, which may be reported to the analysts or recorded for later analysis.

One of the advantages of the detecting engine 150 is that it thresholds both detection filter and coherence scores. Instead of scoring every pixel, as is typically done, the detecting engine 150 computes coherence score for those pixels that having a detection filter score above a nominal threshold, which indicates a potential target. The rationale is that coherence estimation is used in addition to "matched filtering" because it is less likely to report a high score in response to clutter, especially man-made clutter. A convenient example of the detecting engine 150 validates whether a high detection filter score is a real target or likely to be due to clutter by computing coherence score for pixels with modest detection filter scores. The foregoing is particularly advantageous in scenarios in which an enemy, for example, tries to hide a real target with false targets.

Having described examples of the detecting engine 150, generally, the following are convenient examples of the detecting engine 150.

A convenient example of the detecting engine 150 computes the more processing intensive kernel used in the ACE denominator only for a subset of pixels in a hyperspectral scene. The example detecting engine selects only the highest detection filter score pixels for further processing with coherence estimation, and then calculates the coherence score only for those pixels.

A convenient example of the detecting engine 150 does the calculation of standard hyperspectral filters, such as Matched Filter and ACE more efficiently, with fewer mathematical operations when the evaluation of a RX anomaly filter at every pixel is not required.

A convenient example of the detecting engine 150 calculates "matched filters" efficiently for applications that use only detection filter scores to identify detections. Another convenient example of the detecting engine 150 calculates both detection filter and coherence scores efficiently for applications that use both scores to identify detections.

A convenient example of the detecting engine 150 computes ACE iteratively based on MF score.

An example of the detecting engine 150 reduces the number of operations for spectral covariance calculation by using only a fraction of the pixels in the scene, f, to approximate a full scene spectral covariance. Because the purpose of the spectral covariance is to characterize the background and make the MF and ACE scores adaptive to the background, spectral covariance sampling should still characterize the common portions of the scene background.

The detecting engine 150 approximates the full scene spectral covariance by removing outlier pixel contributions to decontaminate the spectral covariance. The detecting engine 150 also conditions the spectral covariance to avoid numerical problems with the spectral covariance inversion. The detecting engine 150 than calculates the spectral covariance using only a fraction of the pixels in the hyperspectral scene. The number of calculations done by the detecting engine 150 is reduced by a factor of f, the fraction of pixels used. Compared to the full scene spectral covariance calculation, spectral covariance sampling by the detecting engine 150 can reduce the number of processing operations by a factor of three to ten.

Advantageously, with fewer operations to perform, examples of the detecting engine 150 can be implemented in processors that are smaller in size, lighter in weight and/or use less power. Such detecting engines are ideal for remote imagining systems, like the one described with reference to FIG. 1.

Figure 4:
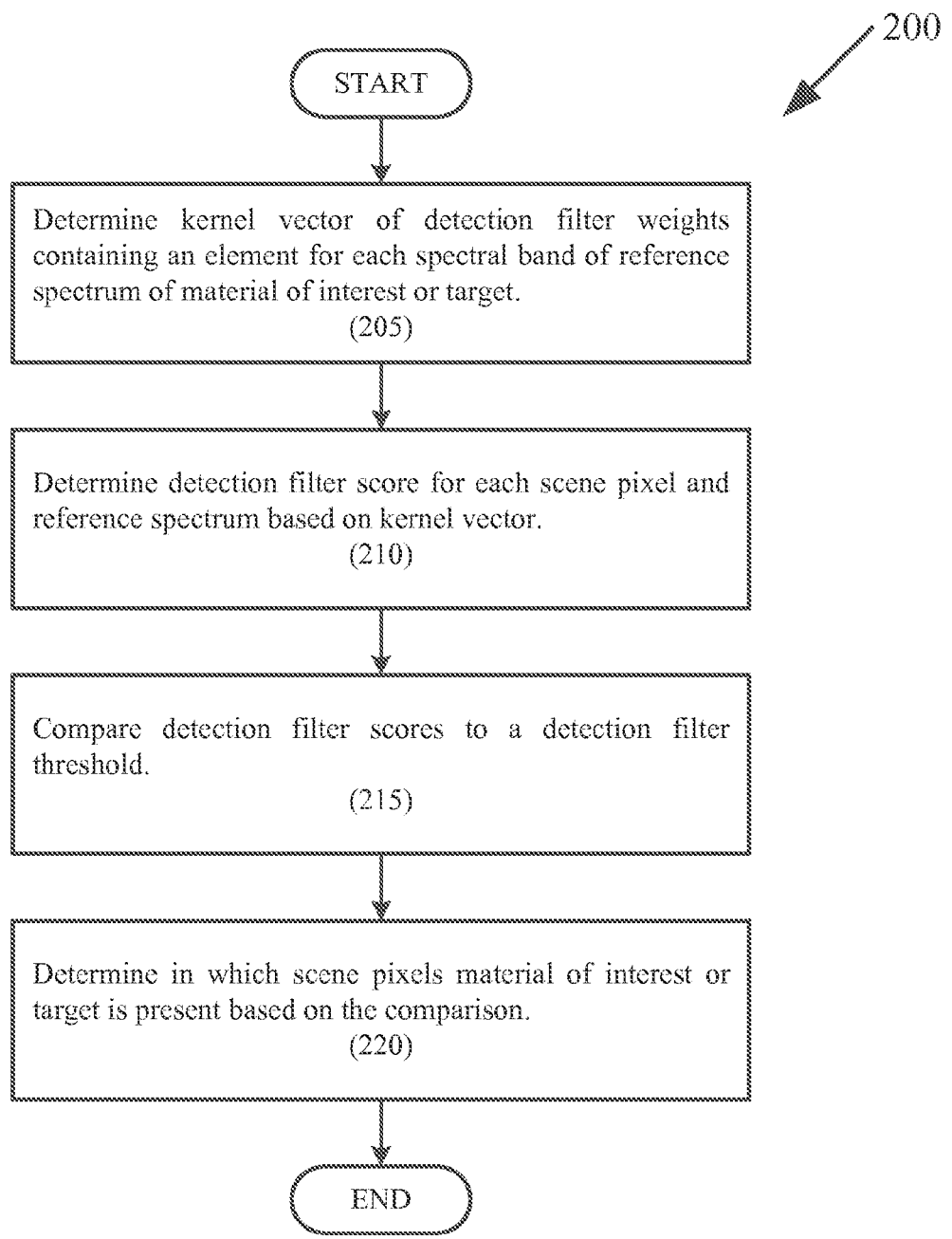
FIG. 4 is a flow chart of an example procedure performed by the detecting engine of FIG. 2.

FIG. 4 shows an example procedure 200 performed by the detecting engine 150 of FIG. 2. The detecting engine 150 is provided with a plurality of reference spectrums each of which includes spectral bands representative of a material, and spectra of a plurality of scene pixels. With respect to a subject reference spectrum of a respective material, the procedure 200 determines (205) a kernel vector of detection filter weights containing an element for each spectral band of a subject reference spectrum.

The procedure 200 determines (210), based on the kernel vector for the subject reference spectrum, a detection filter score for each of the plurality of pixels and subject reference spectrum. The detection filter score is indicative of a likelihood the spectrum of a respective pixel matches the subject reference spectrum associated with the respective material.

The procedure 200 compares (215) the detection filter scores to a detection filter threshold.

The procedure 200 determines (220), based on the comparison, in which of the plurality of pixels in the hyperspectral scene the respective material is present.

The procedure 200 repeats the foregoing (205-220) for each reference spectrum in the plurality of reference spectrums.

Figure 5:
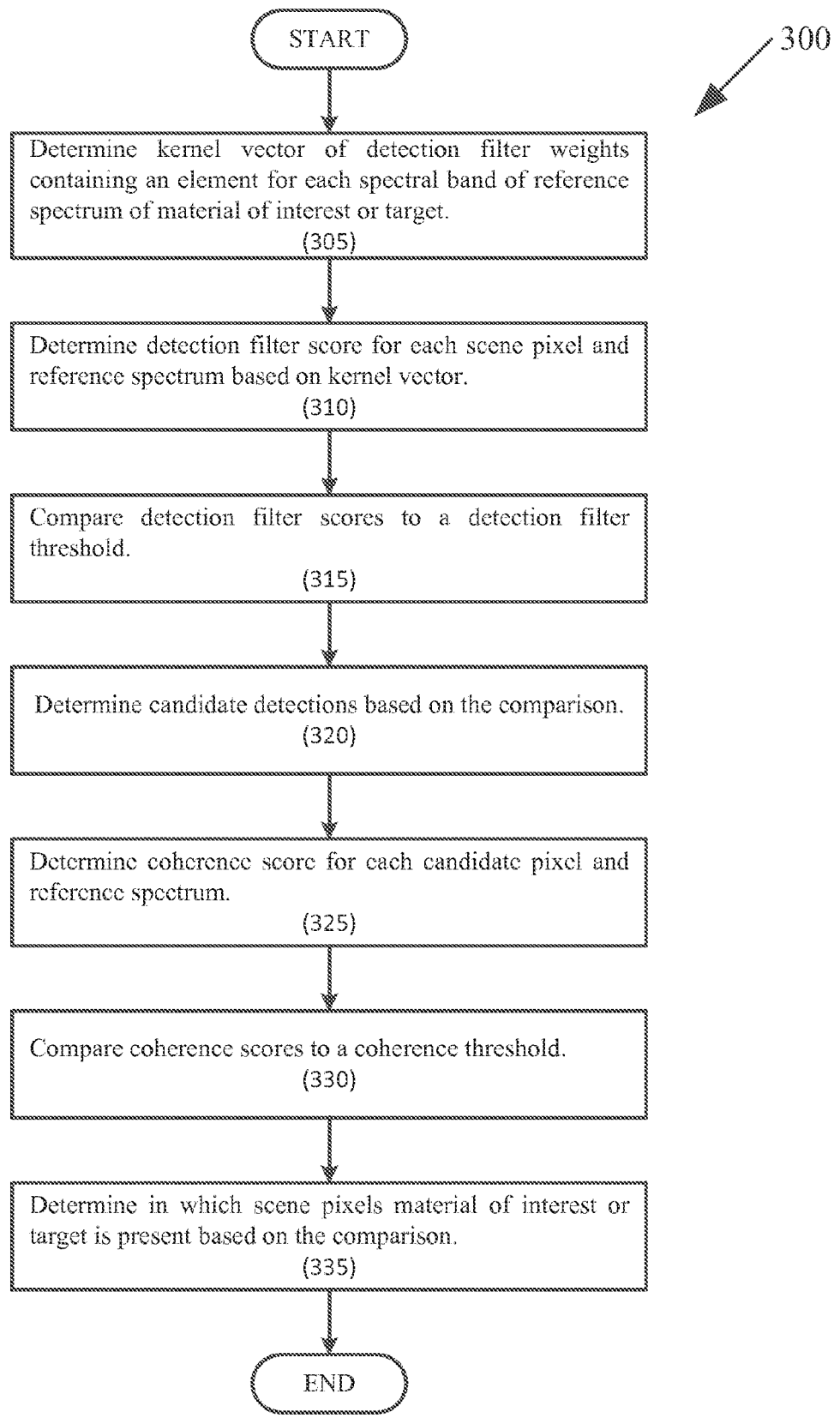
FIG. 5 is a flow chart of an example procedure performed by the detecting engine of FIG. 3.

FIG. 5 shows an example procedure 300 performed by the detecting engine 150 of FIG. 3. The detecting engine 150 is provided with a plurality of reference spectrums each of which includes spectral bands representative of a material, and spectra of a plurality of scene pixels. With respect to a subject reference spectrum of a respective material, the procedure 300 determines (305) a kernel vector of detection filter weights containing an element for each spectral band of a subject reference spectrum.

The procedure 300 determines (310), based on the kernel vector for the subject reference spectrum, a detection filter score for each of the plurality of pixels and subject reference spectrum. The detection filter score is indicative of a likelihood the spectrum of a respective pixel matches the subject reference spectrum associated with the respective material.

The procedure 300 compares (315) the detection filter scores to a detection filter threshold.

The procedure 300 determines (320), based on the comparison, in which of the plurality of pixels in the hyperspectral scene the respective material is present. Pixels in which the respective material is present are candidate detections The procedure 300 determines (325) a coherence score for each of the candidate detections and subject reference spectrum. The coherence score is indicative of a likelihood the spectrum of a respective candidate detection matches the subject spectrum associated with the respective material.

The procedure 300 compares (330) the coherence scores to a coherence threshold.

The procedure 300 determines (335), based on the comparison, in which of the candidate detections the respective material is present.

The procedure 300 repeats the foregoing steps (305-335) for each reference spectrum in the plurality of reference spectrums.

The above-described systems and methods can be implemented in digital electronic circuitry, in computer hardware, firmware, and/or software, e.g., in imaging system 102. The implementation can be as a computer program product (i.e., a computer program tangibly embodied in an information carrier medium). The implementation can, for example, be in a machine-readable storage device for execution by, or to control the operation of, data processing apparatus. The implementation can, for example, be a programmable processor, a computer, and/or multiple computers.

In one example, a computer program can be written in any form of programming language, including compiled and/or interpreted languages, and the computer program can be deployed in any form, including as a stand-alone program or as a subroutine, element, and/or other unit in image processor 100 suitable for use in a computing environment to carry out the features and functions of various examples discussed herein. A computer program can be deployed to be executed on one computer or on multiple computers at one site (e.g., in imaging system 102).

Method steps or operations can be performed as processes by one or more programmable processors executing a computer program to perform functions of various examples by operating on input data and generating output. Method steps can also be performed by and an apparatus can be implemented as special purpose logic circuitry. The circuitry can, for example, be a field programmable gate array (FPGA) and/or an application specific integrated circuit (ASIC). Modules, subroutines, and software agents can refer to portions of the computer program, the processor, the special circuitry, software, and/or hardware that implements that functionality.

Detecting engine 150 may comprise one or more processors suitable for the execution of a computer program include, by way of example, both general and special purpose microprocessors, and any one or more processors of any kind of digital computer. Generally, a processor receives instructions and data from a read-only memory or a random access memory or both. The elements of a computer may comprise a processor for executing instructions and one or more memory devices for storing instructions and data. Generally, a computer can include, can be operatively coupled to receive data from and/or transfer data to one or more mass storage devices (e.g., a memory module) for storing data (e.g., magnetic, magneto-optical disks, or optical disks). The memory may be a tangible non-transitory computer-readable storage medium having computer-readable instructions stored therein for processing images, which when executed by one or more processors (e.g., detecting engine 150) cause the one or more processors to carry out or implement the features and functionalities of various examples discussed herein.

Information carriers suitable for embodying computer program instructions and data include all forms of non-volatile memory, including by way of example semiconductor memory devices. The information carriers can, for example, be EPROM, EEPROM, flash memory devices, magnetic disks, internal hard disks, removable disks, magneto-optical disks, CD-ROM, and/or DVD-ROM disks. The processor and the memory can be supplemented by, and/or incorporated in special purpose logic circuitry.

To provide for interaction with a user, the above described techniques can be implemented on a computing device having a display device. The display device can, for example, be a cathode ray tube (CRT) and/or a liquid crystal display (LCD) monitor, and/or a light emitting diode (LED) monitor. The interaction with a user can, for example, be a display of information to the user and a keyboard and a pointing device (e.g., a mouse or a trackball) by which the user can provide input to the computing device (e.g., interact with a user interface element). Other kinds of devices can be used to provide for interaction with a user. Other devices can, for example, be feedback provided to the user in any form of sensory feedback (e.g., visual feedback, auditory feedback, or tactile feedback). Input from the user can, for example, be received in any form, including acoustic, speech, and/or tactile input.

The above described systems and techniques can be implemented in a distributed computing system that includes a back-end component. The back-end component can, for example, be a data server, a middleware component, and/or an application server. The above described techniques can be implemented in a distributing computing system that includes a front-end component. The front-end component can, for example, be a client computing device having a graphical user interface, a Web browser through which a user can interact with an example implementation, and/or other graphical user interfaces for a transmitting device. The components of the system can be interconnected by any form or medium of digital data communication (e.g., a communication network). Examples of communication networks include a local area network (LAN), a wide area network (WAN), the Internet, wired networks, and/or wireless networks.

The system may be coupled to and/or include clients and servers. A client and a server are generally remote from each other and typically interact through a communication network. The relationship of client and server arises by virtue of computer programs running on the respective computing devices and having a client-server relationship to each other.

Communication networks may include packet-based networks, which can include, for example, the Internet, a carrier internet protocol (IP) network (e.g., local area network (LAN), wide area network (WAN), campus area network (CAN), metropolitan area network (MAN), home area network (HAN)), a private IP network, an IP private branch exchange (IPBX), a wireless network (e.g., radio access network (RAN), 802.11 network, 802.16 network, general packet radio service (GPRS) network, HiperLAN), and/or other packet-based networks. Circuit-based networks may include, for example, the public switched telephone network (PSTN), a private branch exchange (PBX), a wireless network (e.g., RAN, Bluetooth, code-division multiple access (CDMA) network, time division multiple access (TDMA) network, global system for mobile communications (GSM) network), and/or other circuit-based networks.

The computing device in imaging system 102 may include, for example, a computer, a computer with a browser device, a telephone, an IP phone, a mobile device (e.g., cellular phone, personal digital assistant (PDA) device, laptop computer, electronic mail device), and/or other communication devices. The browser device includes, for example, a computer (e.g., desktop computer, laptop computer) with a World Wide Web browser (e.g., INTERNET EXPLORER® available from Microsoft Corporation, of Redmond, Wash.). The mobile computing device includes, for example, a BLACKBERRY® provided by Research In Motion Limited of Waterloo, Ontario, Canada.

"Comprise," "include," and/or plural forms of each are open ended and include the listed parts and can include additional parts that are not listed. "And/or" is open ended and includes one or more of the listed parts and combinations of the listed parts.

Although the above disclosure discusses what is currently considered to be a variety of useful examples, it is to be understood that such detail is solely for that purpose, and that the appended claims are not limited to the disclosed examples, but, on the contrary, are intended to cover modifications and equivalent arrangements that are within the spirit and scope of the appended claims.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

What is claimed is:

1. A method for detecting materials in a hyperspectral scene containing a plurality of pixels, the method comprising:
   in a detecting engine provided with a plurality of reference spectrums each of which includes spectral bands and a spectrum representative of a material, for each reference spectrum of a respective material:
   determining a kernel vector of detection filter weights containing an element for each spectral band of a subject reference spectrum;
   determining, based on the kernel vector for the subject reference spectrum, a detection filter score for each of the plurality of pixels and subject reference spectrum, the detection filter score being indicative of a likelihood the spectrum of a respective pixel matches the subject reference spectrum associated with the respective material;
   comparing the detection filter scores to a threshold; and
   determining, based on the comparison, in which of the plurality of pixels in the hyperspectral scene the respective material is present.

2. The method of claim 1 wherein the pixels determined based on the comparison are candidate detections, the method further comprising:
   determining a coherence score for each of the candidate detections found using the detection filter scores and subject reference spectrum, the coherence score being indicative of a likelihood the spectrum of a respective candidate detection matches the subject spectrum associated with the respective material;
   comparing the coherence scores to a second threshold; and
   determining, based on the comparison, in which of the candidate detections the respective material is present.

3. The method of claim 1 further comprises determining a spectral covariance based on the plurality of pixels in the hyperspectral scene; and wherein the kernel vector for each reference spectrum being determined using the product of a respective reference spectrum and the inverse of the spectral covariance.

4. The method of claim 1 further comprises determining a sample spectral covariance based on a subset of the plurality of pixels in the hyperspectral scene;
and wherein the kernel vector for each reference spectrum being determined using the product of a respective reference spectrum and the inverse of the sample covariance.

5. The method of claim 2 further comprises determining a sample spectral covariance based on a subset of the plurality of pixels in the hyperspectral scene; and wherein the coherence scores being determined using the sample spectral covariance.

6. The method of claim 2 wherein comparing includes combining the detection filter scores and coherence scores into combined scores and comparing the combined scores to the second threshold.

7. A system for detecting materials in a hyperspectral scene containing a plurality of pixels, the system comprising:
a memory having computer executable instructions thereupon;
at least one interface receiving a plurality of reference spectrums each of which includes spectral bands and a spectrum representative of a material;
a detecting engine coupled to the memory and the at least one interface, the computer executable instructions when executed by the detecting engine cause the detecting engine to, for each reference spectrum of a respective material:
determine a kernel vector of detection filter weights containing an element for each spectral band of a subject reference spectrum;
determine, based on the kernel vector for the subject reference spectrum, a detection filter score for each of the plurality of pixels and subject reference spectrum, the detection filter score being indicative of a likelihood the spectrum of a respective pixel matches the subject reference spectrum associated with the respective material;
compare the detection filter scores to a threshold; and
determine, based on the comparison, in which of the plurality of pixels in the hyperspectral scene the respective material is present.

8. The system of claim 7 wherein the pixels determined based on the comparison are candidate detections and wherein the computer executable instructions when executed by the detecting engine further cause the detecting engine to:
determine a coherence score for each of the candidate detections found using the detection filter scores and subject reference spectrum, the coherence score being indicative of a likelihood the spectrum of a respective candidate detection matches the subject spectrum associated with the respective material;
compare the coherence scores to a second threshold; and
determine, based on the comparison, in which of the candidate detections the respective material is present.

9. A tangible non-transitory computer-readable storage medium having computer readable instructions stored therein for detecting materials in a hyperspectral scene containing a plurality of pixels, which when executed by one or more processors provided with a plurality of reference spectrums each of which includes spectral bands and a spectrum representative of a material, cause the one or more processors to, for each reference spectrum of a respective material:
determine a kernel vector of detection filter weights containing an element for each spectral band of a subject reference spectrum;
determine, based on the kernel vector for the subject reference spectrum, a detection filter score for each of the plurality of pixels and subject reference spectrum, the detection filter score being indicative of a likelihood the spectrum of a respective pixel matches the subject reference spectrum associated with the respective material;
compare the detection filter scores to a threshold; and
determine, based on the comparison, in which of the plurality of pixels in the hyperspectral scene the respective material is present.

10. The tangible non-transitory computer-readable storage medium of claim 9 wherein the pixels determined based on the comparison are candidate detections and wherein the computer readable instructions stored therein, which executed by the one or more processors, further:
determine a coherence score for each of the candidate detections found using the detection filter scores and subject reference spectrum, the coherence score being indicative of a likelihood the spectrum of a respective candidate detection matches the subject spectrum associated with the respective material;
compare the coherence scores to a second threshold; and
determine, based on the comparison, in which of the candidate detections the respective material is present.

* * * * *